(12) United States Patent
Goodstine et al.

(10) Patent No.: US 6,288,528 B1
(45) Date of Patent: Sep. 11, 2001

(54) METHOD AND SYSTEM FOR EVALUATING A CONDITION OF A COMBUSTION VESSEL

(75) Inventors: Stephen L. Goodstine, Windsor; Jonathan S. Simon, Pleasant Valley, both of CT (US)

(73) Assignee: Alstom Power Inc., Windsor, CT (US)

( * ) Notice: Subject to any disclaimer, the term of this patent is extended or adjusted under 35 U.S.C. 154(b) by 0 days.

(21) Appl. No.: 09/313,909

(22) Filed: May 18, 1999

(51) Int. Cl.$^7$ .............................. G01N 27/20; G01R 1/04
(52) U.S. Cl. ..................... 324/71.1; 324/693; 324/700; 324/715; 324/718; 324/71.2
(58) Field of Search .................... 324/693, 699, 324/700, 713, 715, 716, 718, 71.1, 71.2

(56) References Cited

U.S. PATENT DOCUMENTS

| | | |
|---|---|---|
| 1,895,643 | 1/1933 | Putnam . |
| 3,721,897 | 3/1973 | Edling . |
| 4,048,558 | 9/1977 | Goodman . |
| 4,982,154 | 1/1991 | Schwabe et al. . |
| 5,008,628 * | 4/1991 | Krigmont et al. ................ 324/693 |
| 5,217,304 | 6/1993 | Ortiz . |
| 5,332,961 * | 7/1994 | Hammerle ........................ 324/700 |
| 5,486,767 | 1/1996 | Schwabe et al. . |

FOREIGN PATENT DOCUMENTS 1433803    4/1976   (GB) .

* cited by examiner

Primary Examiner—Glenn W. Brown
(74) Attorney, Agent, or Firm—Russell W. Warnock

(57) ABSTRACT

There is provided a method and system for evaluating a condition of a surface of a combustion vessel exposed to deposition thereon of a material released during a combustion of a fuel in the combustion vessel during a combustion process. The method preferably comprises the steps of imposing a current on an electrical network arranged relative to the combustion vessel and having at least one electrode and thereafter detecting at least one characteristic of the electrical network during the step of imposing a current on the electrical network. The method further includes the step of evaluating a condition of the deposition exposed surface based upon the at least one detected characteristic of the electrical network.

17 Claims, 3 Drawing Sheets

METHOD AND SYSTEM FOR EVALUATING A CONDITION OF A COMBUSTION VESSEL

BACKGROUND OF THE INVENTION

The present invention relates to a method and system for evaluating a condition of a combustion vessel and, more particularly to a method and system for evaluating a condition of a combustion vessel as a function of a detected electrical characteristic of the combustion vessel.

One condition of a combustion vessel which is often of interest is the accumulation of combustion related material such as ash based combustion byproduct on deposition exposed surfaces of the vessel. Another related condition which is also often of interest is the loss or wastage of such deposition exposed surfaces or other structure of the combustion vessel which results from the relatively high temperatures and other process conditions often present in combustion vessels such as fossil fuel-fired furnaces.

The fouling of heat transfer surfaces due to the deposition of slag and other constituents of the fly ash generated during fossil fuel combustion is a problem which operators of fossil fuel fired furnaces continuously face. The cumulative reduction in the heat transfer coefficients on the deposition exposed surfaces of the furnace changes the heat distribution within the furnace and reduces the overall furnace efficiency. Further fouling of these surfaces eventually impairs the efficiency of any power generating unit comprising the furnace. Moreover, the accumulation of slag or other deposits on the surfaces frequently accelerates the corrosion of the metal which typically comprises such surfaces.

Several methods have been proposed for evaluating conditions such as the two aforementioned conditions in combustion vessels. U.S. Pat. No. 4,176,554 discloses a method for evaluating a temperature profile of a kiln which includes the steps of obtaining a temperature profile of the kiln based upon temperature information provided by a plurality of thermocouples. U.S. Pat. No. 5,615,953 discloses a system for obtaining a temperature profile of a bank of tubes of a fossil fuel-fired boiler in order to determine the amount of build up on the tubes. A series of temperature readings are taken at intervals along the length of an extension arm, such as a sootblower lance, which is extended near the tube banks of a boiler. The temperature readings are integrated to form a temperature profile from which conclusions may be drawn concerning the accumulation of the tube banks of the boiler.

Although there has been demonstrated the desirability of a method and a system for reliably monitoring selected conditions of a combustion vessel, such a method and system has not yet been proposed. Accordingly, the need still exists for a method and a system for reliably monitoring selected conditions of a combustion vessel.

SUMMARY OF THE INVENTION

It is one object of the present invention to provide a method for reliably monitoring selected conditions of a combustion vessel.

It is another object of the present invention to provide a system for reliably monitoring selected conditions of a combustion vessel.

According to one aspect of the present invention, there is provided a method for evaluating a location of interest of a combustion vessel. The method preferably comprises the steps of imposing a current on an electrical network, the electrical network having at least one electrode and being situated relative to the combustion vessel such that properties of the electrical network are influenced by the operation of the combustion vessel. The method further preferably comprises the step of detecting at least one characteristic of the electrical network during the step of imposing a current on the electrical network. The method additionally includes the step of evaluating a condition of the combustion vessel based upon the at least one detected characteristic of the electrical network.

According to one variation of this aspect of the present invention, a fossil fuel is combusted during the combustion process in the combustion vessel and the step of evaluating a condition of the combustion vessel surface includes evaluating the at least one detected characteristic of the electrical network as an indicator of a characteristic of a surface of the combustion vessel. In a further refinement of this one variation, in the event that the material released during the combustion process is ash based combustion byproduct, the step of evaluating the at least one detected characteristic of the electrical network as an indicator of a characteristic of the surface of the combustion vessel surface includes evaluating the at least one detected characteristic of the electrical network as an indicator of a reduction of heat flux.

In yet another feature of this one variation of the above noted method of the present invention, the step of evaluating the at least one detected characteristic of the electrical network as an indicator of the reduction of heat flux includes evaluating a detected resistance value in the electrical network which is relatively greater than a baseline resistance value existing at a baseline time prior to the imposition of a current on the electrical network during the step of imposing of a current on the electrical network as an indicator that the reduction of heat flux is different than the heat flux at the baseline time.

According to another aspect of the present invention, there is provided a system for evaluating a condition of a surface of a combustion vessel exposed to deposition thereon of a material released during a combustion of a fuel in the combustion vessel during a combustion process comprising means for imposing a current on an electrical network having at least one electrode and means for detecting at least one characteristic of the electrical network during the step of imposing a current on the electrical network. The system also includes means for evaluating a condition of the deposition exposed surface based upon the at least one detected characteristic of the electrical network.

In the event that the combustion vessel is operable to combust a fossil fuel during the combustion process, the system preferably includes, in one variation thereof, means for evaluating a condition of the combustion vessel surface which is operable to evaluate the at least one detected characteristic of the electrical network as an indicator of a characteristic of the deposition on the combustion vessel surface. Additionally, if the material released during the combustion process is ash based combustion byproduct, the means for evaluating the at least one detected characteristic of the electrical network as an indicator of a characteristic of the deposition on the combustion vessel surface is, in one variation thereof operable to evaluate the at least one detected characteristic of the electrical network as an indicator of the reduction of heat flux.

A further variation of the system preferably includes the feature that the means for evaluating the at least one detected characteristic of the electrical network as an indicator of the reduction of heat flux is operable to evaluate a detected resistance value in the electrical network which is different than a baseline resistance value existing at a baseline time prior to the imposition of a current on the electrical network while a current is imposed on the electrical network as an indicator that the depth of deposition on the combustion vessel surface is relatively greater than the depth of deposition at the baseline time. Furthermore, the means for detecting, in this variation of the system, is preferably operable to detect a resistance value and the means for evaluating includes means for comparing the at least one detected characteristic with at least one predetermined resistance value.

According to a further aspect of the present invention, there is provided a method for iteratively imposing, during respective current imposing intervals, a current on an electrical network arranged relative to a combustion vessel and iteratively detecting a respective property of the electrical network such as, for example, a resistance or a voltage value of the electrical network, in association with each respective imposition of a current on the electrical network. This iterative method also includes the step of comparing each detected resistance/voltage value with a comparison stored resistance/voltage value set having at least one resistance/voltage value stored in a database of predetermined resistance/voltage values, each resistance/voltage value of the comparison stored resistance/voltage value set characterizing the combustion vessel surface at a time other than the respective current imposing interval.

According to yet another aspect of the present invention, there is provided a method operable to evaluate a combustion vessel in which a combustion process occurs which contributes to a slagging process in which slag accrues on surfaces of the combustion vessel. This method includes the step of evaluating includes determining that a condition of slagging exists in the combustion vessel in the event that: (1) the interval between the reference time and the milestone time is less than a predetermined magnitude and (2) a variation exists between the reference resistance characteristic and the milestone resistance characteristic.

The step of evaluating of this further method of the present invention also preferably includes determining that a condition of slagging exists in the combustion vessel in the event that: (1) the interval between the reference time and the milestone time is less than a predetermined magnitude and (2) a variation greater than a predetermined magnitude exists between the reference resistance characteristic and the milestone resistance characteristic. Moreover, in the application of the method in connection with a combustion vessel including tubes for circulating a heat exchange medium therein while the tubes are exposed to is increased temperatures during the combustion process, the step of evaluating includes determining that a condition of a build up of deposition material on the firesides of the tubes exists in the event that: (1) the interval between the reference time and the milestone time is greater than a predetermined magnitude and (2) a variation greater than a predetermined magnitude exists between the reference resistance characteristic and the milestone resistance characteristic.

In a variation of the method for evaluating a condition of a combustion vessel in accordance with the yet another aspect of the present invention, the method includes detecting at a milestone time a resistance characteristic of a electrical network having at least two electrodes disposed relative to a portion of interest of the combustion vessel for passing a current therethrough to thereby enable the milestone resistance characteristic to be obtained, the portion of interest of the combustion vessel being characterized by a milestone temperature at the milestone time and evaluating the milestone resistance characteristic. The evaluation of the milestone reference characteristic includes evaluating this characteristic with respect to a reference resistance characteristic of the electrical network which characterizes the electrical network at a reference time different from the milestone time during which the temperature of the portion of interest of the combustion vessel varies at the most ten percent (10%) from its milestone temperature, the step of evaluating including determining that the portion of interest of the combustion vessel has undergone a loss of material in the event that the interval between the reference time and the milestone time is greater than a predetermined interval.

DETAILED DESCRIPTION OF THE PREFERRED EMBODIMENTS

Figure 1:
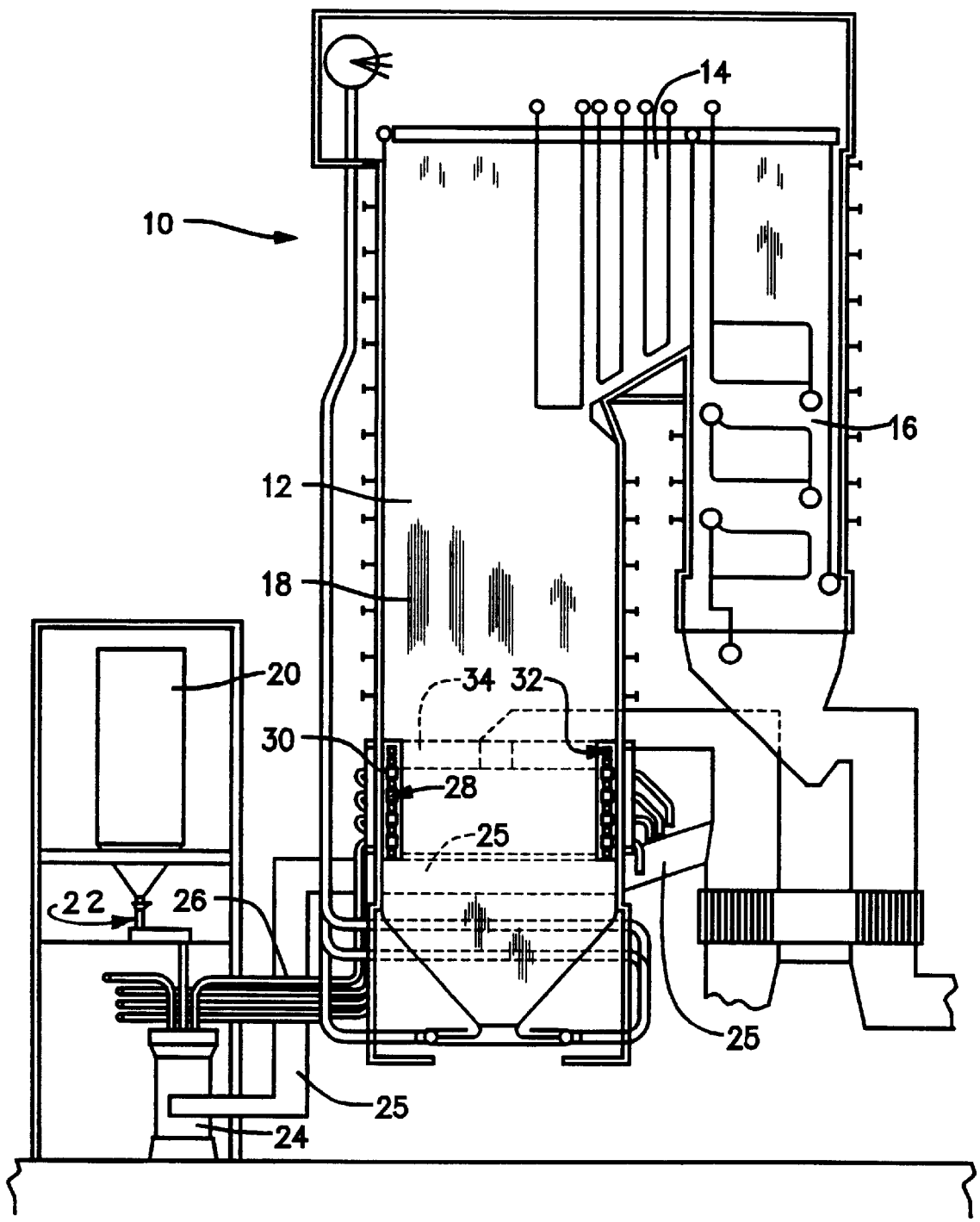
FIG. 1 is a schematic front plan view of an exemplary combustion vessel a condition of which is evaluated in accordance with the method of the present invention in the form of a power generating unit including a fossil fuel-fired furnace.

FIG. 1 illustrates an exemplary power generating unit 10 having a fossil fuel fired combustion vessel in the form of a furnace 12 and additionally including a horizontal gas pass 14 and a back pass 16. The furnace 12 has a fireside delimited by a plurality of water wall tubes 18 in which a heat exchange medium—namely, water—is circulated and which is converted into steam as a result of heating of the tubes 18 during the combustion of a fossil fuel such as, for example, coal, in the furnace 12. The power generating unit 10 may include other conventional elements such as, for example, a turbine (not illustrated) for generating electricity under the motive action of steam passed thereover. Moreover, the horizontal gas pass 14 and the back pass 16 may comprise selected arrangements of economizers, superheaters, and reheaters.

A coal feed apparatus 20 is operable to feed coal to a feeder 22 which controls the rate of coal flow to a pulverizer 24. Hot primary combustion air is also fed to the pulverizer 24 via a duct 25 and this air carries pulverized coal through and out of the pulverizer 24 and thereafter through coal pipes 26 to several groups of coal nozzles 28. Each group of coal nozzles 28 is mounted in a respective tangential firing windbox 30 which also each support a group of secondary air nozzles 32. The windboxes 30 introduce controlled flows of air and pulverized coal into the fireside of the furnace 12 to effect the formation therein of a rotating fireball. The rotating fireball is a combustion process of the type which results in the release of a material which contributes to depositions on the fireside surfaces of the water wall tubes 18—namely, carbon based combustion byproduct is released which builds up as slag on the fireside surfaces of the water wall tubes 18.

Figure 2:
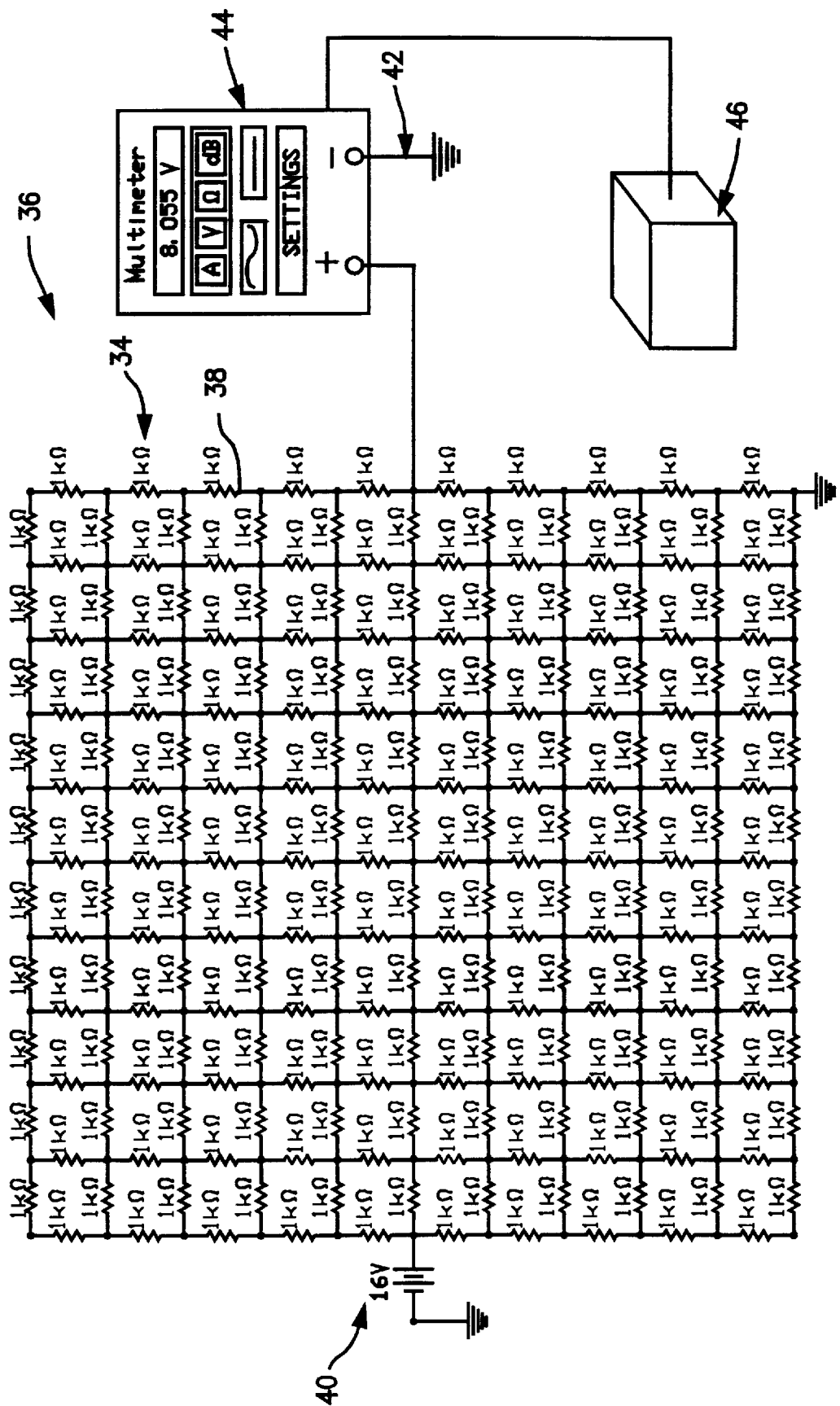
FIG. 2 is an enlarged front plan view of a portion of the water wall tubes of the fossil fuel-fired furnace shown in FIG. 1 and showing, in simulated manner, an instantaneous resistance characteristic of an electrical network arranged with respect to the water wall tube portion at a reference or baseline time.

FIG. 2 is a schematic representation of an electrical network 34 arranged relative to a portion of interest 36 of a fireside surface of several of the water wall tubes 18. The electrical network 34 may be simulated as a plurality of resistors 38 arranged in series/parallel combination. The resistors 38 are of equal value. In an actual portion of a wall panel comprising the water wall tubes 18, any selected portion of a metal tube can be regarded as a resistor. For example, each attachment pin of the type typically employed in the assembly of a series of water wall tubes together into a wall panel may be viewed as a lead or electrode through which current can be imposed with any selected group of adjacent pins being deemed as an electrical network such as the electrical network 34 from which electrical resistance can be measured when a current is imposed or impressed through one selected pin as an input and grounded through another selected pin as a ground.

The method is generally implemented by imposing one or more current patterns through leads or electrodes forming the electrical network 34, in a prescribed manner which will be described in more detail shortly, detecting a characteristic of the electrical network 34—namely, voltage measurements corresponding to each imposed current, and evaluating a condition of the furnace 12 based upon the detected characteristic of the electrical network 34. Each iteration of imposing a current on the electrical network 34 is accomplished by iteratively connecting one or more selected electrodes or leads to a voltage source 40 and connecting one or more other selected electrodes or leads to a ground 42. A voltmeter 44 is connected to a respective resistor node to measure the voltage in connection with each imposed current pattern. Another type of data display device may be substituted for the voltmeter 44 and a data storage and manipulation device such as, for example, a microprocessor 46, may be substituted for or coupled with the voltmeter 44.

In one version by which the method is implemented, the method includes the step of detecting, at one or more predetermined times, an instantaneous resistance characteristic of the electrical network 34. This can be accomplished, for example, by imposing a current on the electrical network 34 with any selected combination of electrodes of the electrical network functioning each functioning as a respective input or output to ground for the imposed current. Thus, one step of the method includes detecting, at a milestone time M1, a milestone resistance characteristic MILECHAR of the electrical network 34. The milestone resistance characteristic MILECHAR is detected by the voltmeter 44 at the milestone time M1 and the detected resistance characteristic is, additionally, displayed by the voltmeter and, if desired, transmitted to the microprocessor 46 for storage and manipulation thereby. It is noted that the portion 36 of the furnace 12 is characterized by an instantaneous temperature at the time of each detection of a resistance characteristic; for example, the portion 36 is characterized by a milestone temperature TEMP1 at the milestone time M1.

The method also includes the step of evaluating the milestone resistance characteristic MILECHAR with respect to a reference resistance characteristic REFCHAR of the electrical network 34. The reference resistance characteristic REFCHAR characterizes the electrical network 34 at a reference or baseline time REFTIME different from the milestone time M1 during which the instantaneous temperature of the portion 36 of the water wall tubes 18 is different than its milestone temperature TEMP1. In this version of the method of the present invention, the step of evaluating including evaluating at least one of: (a) the interval between the reference time REFTIME and the milestone time M1 and (b) a variation property of the milestone resistance characteristic MILECHAR and the reference resistance characteristic REFCHAR with respect to each other. The variation property of the milestone resistance characteristic MILECHAR and the reference resistance characteristic REFCHAR with respect to each other may be either a property in which there is no variation between the milestone resistance characteristic MILECHAR and the reference resistance characteristic REFCHAR (i.e., the resistance characteristics are equal to one another) or a property in which there is a variation between the milestone resistance characteristic MILECHAR and the reference resistance characteristic REFCHAR.

The evaluation performed in accordance with the method of the present invention is guided by certain premises which take into account the differences between or among conditions of the furnace 12 as evidenced, for example, by the manner in which these conditions manifest themselves with respect to uniform or varying heat flux conditions in the furnace or by the rate at which a condition manifests itself. In this regard, the step of evaluating may include, in one variation of the method of the present invention, determining that a condition of slagging exists in portion 36 of the water wall tubes 18 in the event that: (1) the interval between the reference time REFTIME and the milestone time M1 is less than a predetermined magnitude and (2) a variation greater than a predetermined magnitude exists between the reference resistance characteristic REFCHAR and the milestone resistance characteristic MILECHAR. This determination capitalizes on the premise that a change in resistance within a relatively short term (i.e., within an interval between the reference time REFTIME and the milestone time M1 less than a predetermined magnitude) as well as a heat flux of at least a minimum magnitude (i.e., a variation greater than a predetermined magnitude between the reference characteristic REFCHAR and the milestone resistance characteristic MILECHAR) signifies the existence of slagging.

As another illustration of an implementation of the evaluating step of the method of the present invention, the evaluating step may determine that a condition of an internal build up of material in the interior of the tubes exists in the event that: (1) the interval between the reference time REFTIME and the milestone time M1 is greater than a predetermined magnitude and (2) a variation greater than a predetermined magnitude exists between the reference resistance characteristic REFCHAR and the milestone resistance characteristic MILECHAR. This determination that internal tube deposition is present capitalizes on the premise that a relatively long term change (a change detected only after the passage of an interval between the reference time REFTIME and the milestone time M1 greater than a predetermined magnitude) and detectable only in the presence of a heat flux (i.e., a variation greater than a predetermined magnitude exists between the reference resistance characteristic REFCHAR and the milestone resistance characteristic MILECHAR) signals a change in the internal deposition characteristic of the observed water wall tube or tubes.

As a further illustration of an implementation of the evaluating step of the method of the present invention, the step of evaluating the detected characteristic of the portion 36 of the water wall tubes 18 can include evaluating the milestone resistance characteristic MILECHAR with respect to the reference resistance characteristic REFCHAR with the reference time REFTIME at which the reference resistance characteristic REFCHAR is measured being selected such that the temperature of the portion 36 of the water wall tubes 18 at this time varies at the most ten percent (10%) from its milestone temperature TEMP1 existing at the milestone time M1. In this implementation of the method, the step of evaluating includes determining that the portion 36 of the water wall tubes 18 has undergone a loss of material in the event that the interval between the reference time REFTIME and the milestone time M1 is greater than a predetermined interval. This determination capitalizes on the premise that metal loss in a tube is a relatively long term change (i.e., the interval between the reference time REFTIME and the milestone time M1 is greater than a predetermined interval) which is detectable under uniform or substantially uniform heat flux conditions (i.e., the temperature of the portion 36 of the water wall tubes 18 varies at the most ten percent (10%) from its milestone temperature TEMP1).

Figure 3:
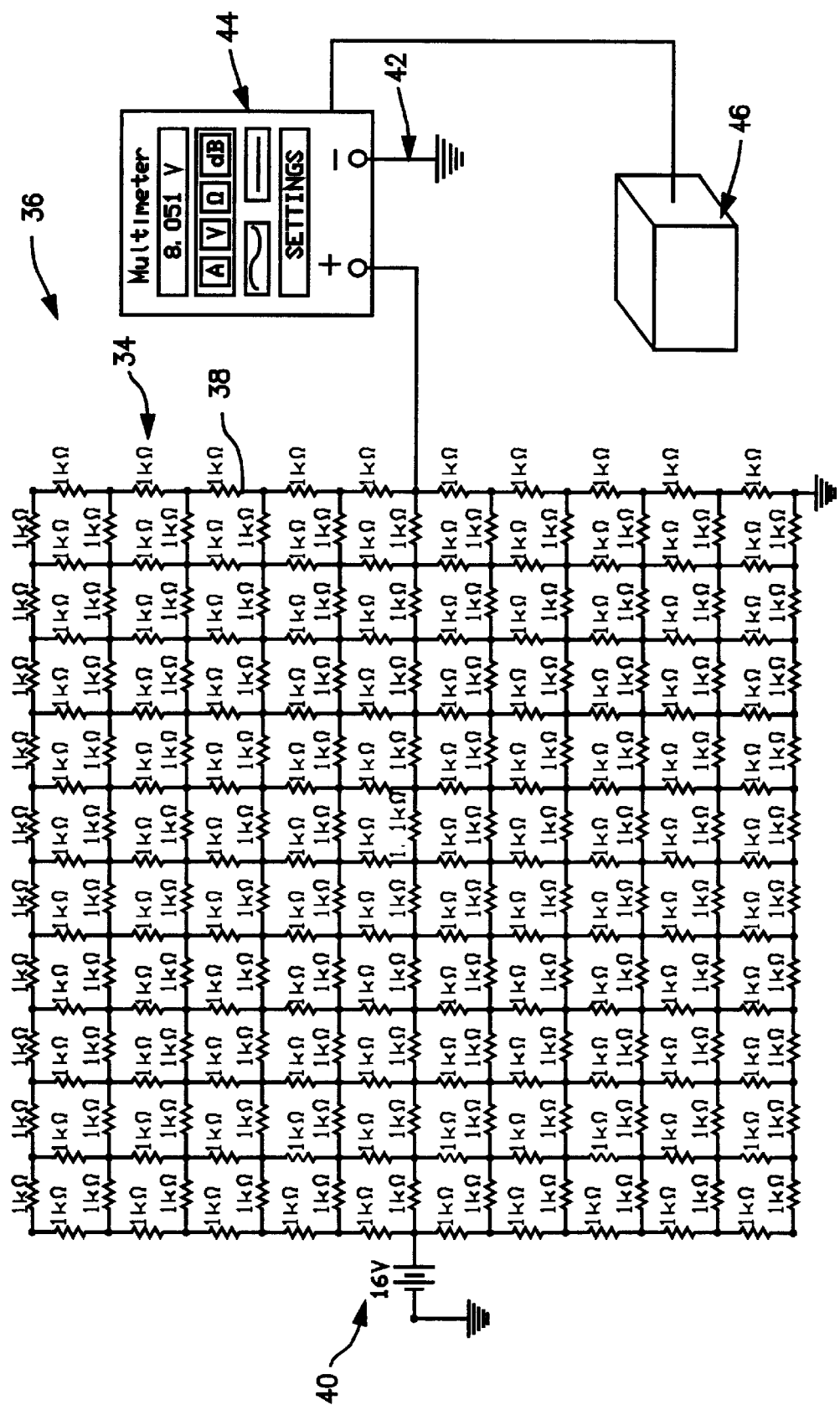
FIG. 3 is an enlarged front plan view of the portion of the water wall tubes of the fossil fuel-fired furnace shown in FIG. 2 and showing, in simulated manner, an instantaneous resistance characteristic of the electrical network arranged with respect to the water wall tube portion at a milestone time.

Reference is made to FIGS. 2 and 3 as an illustration of the operation of the electrical network 34 and the associated components of the system of the present invention. As seen in FIG. 2, during a reference or baseline time REFTIME, a current is imposed by the voltage source 40 at a selected electrode on the left hand side of the electrical network 34. Another selected electrode, in the lower right hand corner of the electrical network 34, is connected to the ground 42. The voltmeter 44 is coupled to yet another selected electrode and detects a reference resistance characteristic REFCHAR having a value of 8.055 volts. It is assumed in this illustration of the operation of the electrical network 34 that the portion 36 of the water wall tubes 18 has an instantaneous temperature of a determinate value at the respective reference or baseline time REFTIME.

As now seen in FIG. 3, during a milestone time M1 which is at a time other than the respective reference or baseline time REFTIME at which the reference resistance characteristic REFCHAR is detected as shown in FIG. 2, another current is imposed on the electrical network 34 and the voltmeter 44 now detects a milestone reference characteristic MILECHAR having a value of 8.051 volts. It is assumed in this illustration of the operation of the electrical network 34 that the portion 36 of the water wall tubes 18 has an instantaneous temperature of a determinate value at the milestone time M1 different than the instantaneous temperature at the respective reference or baseline time REFTIME.

The difference between the respective reference resistance characteristic REFCHAR and the milestone resistance characteristic MILECHAR is a decrease in the voltage of four (4) millivolts (a decrease of 0.05% in the detected voltage of the electrical network 34). This decrease in voltage is attributable to an increase in the resistance at one particular resistor 38, generally in the middle of the electrical network 34, from a value of 1.0 ohms, as shown in FIG. 2, to a new value of 1.1 ohms, as shown in FIG. 3, thus comprising a resistance increase at this one resistor of (1.1 ohms minus 1.0 ohms=0.1 ohms or [(0.1)/(1.0) or ten percent (10%)]. The increase in resistance at the one particular resistor 38 may be attributable, for example, to a metal loss of a water wall tube at or proximate to the one particular resistor 38. The exemplary implementation of one variation of the method of the present invention just described thus illustrates that the method of the present invention can be implemented in a combustion vessel which includes a waterwall having a plurality of tubes for circulation therethrough of a heat transfer medium with the specific implementation that the step of evaluating includes determining that a condition of wastage of the waterwall exists in the event that: (1) the variation between the temperature at the reference time and the temperature at the milestone time is no greater than a maximum variation and (2) a variation exists between the reference resistance characteristic and the milestone resistance characteristic.

While several embodiments of the invention have been shown, it will be appreciated that modifications thereof, some of which have been alluded to hereinabove, may still be readily made thereto by those skilled in the art. It is therefore intended by the appended claims to cover the modifications alluded to herein as well as all the other modifications which fall within the true spirit and scope of the invention.

We claim:

1. A method for evaluating a condition of a combustion vessel, the combustion vessel having a combustion area enclosing structure which encloses a combustion area wherein combustion occurs, the combustion area enclosing structure having a fireside surface which is directly exposed to heat and other products resulting from combustion activity occurring in the combustion area and another surface exteriorly of the fireside surface which is only indirectly exposed to the influence of heat and other products resulting from combustion activity in that the fireside surface is intermediate the combustion area and the other surface, the method comprising the steps of:

providing an electrical network comprised of at least one electrode and the fireside surface, the electrode having a connection on the other surface of the combustion vessel for connecting the electrode to an electrical current source for passage of a current from the electrical current source to the electrode along a current supply path which is continuously exterior of the fireside surface and the current being passed to the fireside surface solely via the other surface of the combustion area enclosing structure, the electrical network being situated relative to the combustion activity in the combustion vessel such that properties of the electrical network are influenced by the combustion activity in the combustion vessel;

imposing a current on the electrode;

detecting at least one characteristic of the electrical network during the step of imposing a current on the electrical network; and evaluating a condition of the fireside surface based upon the at least one detected characteristic of the electrical network.

2. A method according to claim 1 wherein a plurality of waterwall tubes comprise the fireside surface and a fossil fuel is combusted during the combustion activity in the combustion vessel and the step of evaluating a condition of the fireside surface includes evaluating the at least one detected characteristic of the electrical network as an indicator of a characteristic of a loss of material of a waterwall tube of the combustion vessel.

3. A method according to claim 1 and further comprising:

iteratively imposing a current on the electrical network;

iteratively detecting a value of a respective property of the electric network in association with each respective imposition of a current on the electrical network, the property value of the electrical network including at least one of a resistance value of the electrical network and a voltage value of the electrical network; and comparing each detected property value of the electrical network with a comparison stored value set having at least one value of the respective property of the electrical network stored in a database of predetermined values, each predetermined value of the comparison stored value set representing a desired property value.

4. A method according to claim 1 wherein a fossil fuel is combusted during the combustion activity in the combustion vessel and one of the products of the combustion activity to which the fireside surface is exposed is a combustion product which deposits on the fireside surface and the step of evaluating a condition of the fireside surface includes evaluating the at least one detected characteristic of the electrical network as an indicator of a characteristic of the deposition on the fireside surface of the combustion vessel.

5. A method according to claim 4 wherein a carbon based combustion byproduct is released during the combustion activity which contributes to deposition on the fireside surface of the combustion vessel and the step of evaluating the at least one detected characteristic of the electrical network as an indicator of a characteristic of the deposition on the fireside surface includes evaluating the at least one detected characteristic of the electrical network as an indicator of a reduction of heat flux.

6. A method according to claim 5 wherein the step of evaluating the at least one detected characteristic of the electrical network as an indicator of the reduction of heat flux includes evaluating a detected resistance value in the electrical network which is different than a minimum difference from a baseline resistance value existing at a baseline time prior to the imposition of a current on the electrical network during the step of imposing of a current on the electrical network as an indicator that there has been a reduction of heat flux relative to the heat flux at the baseline time.

7. A system for evaluating a condition of a location of interest of a combustion vessel, the combustion vessel having a combustion area enclosing structure which encloses a combustion area wherein combustion occurs, the combustion area enclosing structure having a fireside surface which is directly exposed to heat and other products resulting from combustion activity occurring in the combustion area and another surface exteriorly of the fireside surface which is only indirectly exposed to the influence of heat and other products resulting from combustion activity in that the fireside surface is intermediate the combustion area and the other surface, the method comprising the steps of:
  means forming an electrical network comprised of at least one electrode and the fireside surface, the electrode having a connection on the other surface of the combustion vessel for connecting the electrode to an electrical current source for passage of a current from the electrical current source to the electrode along a current supply path which is continuously exterior of the fireside surface and the current being passed to the fireside surface solely via the other surface of the combustion area enclosing structure, the electrical network being situated relative to the combustion activity in the combustion vessel such that properties of the electrical network are influenced by the combustion activity in the combustion vessel;
  means for imposing a current on an electrical network having at least one electrode;
  means for detecting at least one characteristic of the electrical network during the step of imposing a current on the electrical network; and
  means for evaluating the location of interest based upon the at least one detected characteristic of the electrical network.

8. A system according to claim 7 wherein the combustion vessel is operable to combust a fossil fuel during the combustion activity and a plurality of waterwall tubes comprise the fireside surface of the combustion vessel and the means for evaluating the location of interest is operable to evaluate the at least one detected characteristic of the electrical network as an indicator of a heat transfer characteristic of the location of interest of the combustion vessel whereby a loss of material of at least one of the waterwall tubes of the combustion vessel can be determined.

9. A method according to claim 7 wherein the step of evaluating the milestone resistance characteristic with respect to a reference characteristic of the electrical network includes evaluating the milestone resistance characteristic with respect to a reference resistance characteristic of the electrical network which characterizes the electrical network at a reference time different from the milestone time during which reference time the temperature of the portion of interest of the combustion vessel varies at the most ten percent (10%) from its milestone temperature and the step of evaluating including determining that the portion of interest of the combustion vessel has undergone a loss of material in the event that the interval between the reference time and the milestone time is greater than a predetermined interval magnitude.

10. A method according to claim 7 wherein the combustion vessel includes a waterwall having a plurality of tubes for circulation therethrough of a heat transfer medium and the step of evaluating includes determining that a condition of wastage of the waterwall exists in the event that: (1) the variation between the temperature at the reference time and the temperature at the milestone time is no greater than a maximum variation and (2) a variation exists between the reference resistance characteristic and the milestone resistance characteristic.

11. A system according to claim 7 wherein a carbon based combustion byproduct is released during the combustion process and the means for evaluating the at least one detected characteristic of the electrical network is operable to evaluate the at least one detected characteristic of the electrical network as an indicator of a change of heat flux.

12. A system according to claim 11 wherein the combustion vessel includes a waterwall having a plurality of tubes for the passage of a heat exchange medium therethrough and the means for evaluating the at least one detected characteristic of the electrical network as an indicator of a change of heat flux is operable to evaluate a detected resistance value in the electrical network which is different greater than a minimum difference than a baseline resistance value existing at a baseline time prior to the imposition of a current on the electrical network as an indication of at least one of a relative increase in the deposition on the combustion vessel surface and a relative reduction in a thickness dimension of the waterwall.

13. A system according to claim 11 wherein the means for detecting is operable to detect a resistance value and the means for evaluating includes means for comparing the at least one detected characteristic with at least one predetermined resistance value.

14. A method for evaluating a condition of a location of interest of a combustion vessel, the combustion vessel having a combustion area enclosing structure which encloses a combustion area wherein combustion occurs, the combustion area enclosing structure having a fireside surface which is directly exposed to heat and other products resulting from combustion activity occurring in the combustion area and another surface exteriorly of the fireside surface which is only indirectly exposed to the influence of heat and other products resulting from combustion activity in that the fireside surface is intermediate the combustion area and the other surface, the method comprising the steps of:

providing an electrical network comprised of at least one electrode and the fireside surface, the electrode having a connection on the other surface of the combustion vessel for connecting the electrode to an electrical current source for passage of a current from the electrical current source to the electrode along a current supply path which is continuously exterior of the fireside surface and the current being passed to the fireside surface solely via the other surface of the combustion area enclosing structure, the electrical network being situated relative to the combustion activity in the combustion vessel such that properties of the electrical network are influenced by the combustion activity in the combustion vessel;

detecting at a milestone time a resistance characteristic of the electrical network, the location of interest of the combustion vessel being characterized by a milestone temperature at the milestone time; and evaluating the milestone resistance characteristic with respect to a reference resistance characteristic of the electrical network which characterizes the electrical network at a reference time different from the milestone time, the step of evaluating including evaluating both a variation property relating to a temperature at the reference time and a temperature at the milestone time and at least one of the interval between the reference time and the milestone time and a variation property of the milestone resistance characteristic and the reference resistance characteristic with respect to each other.

15. A method according to claim 14 wherein the combustion vessel includes tubes for circulating a heat exchange medium therein while the tubes are exposed to increased temperatures during the combustion process and the step of evaluating includes determining that a condition of an internal build up of material on the interior of the tubes exists in the event that: (1) the interval between the reference time and the milestone time is greater than a predetermined magnitude and (2) a variation greater than a predetermined magnitude exists between the reference resistance characteristic and the milestone resistance characteristic.

16. A method according to claim 14 wherein during which the temperature of the location of interest of the combustion vessel is different than its milestone temperature, the combustion activity in the combustion vessel contributes to a slagging process in which slag accrues on the fireside surface of the combustion vessel, and the step of evaluating includes determining that a condition of slagging exists in the combustion vessel in the event that: (1) the interval between the reference time and the milestone time is less than a predetermined magnitude and (2) a variation exists between the reference resistance characteristic and the milestone resistance characteristic.

17. A method according to claim 16 wherein the step of evaluating includes determining that a condition of slagging exists in the combustion vessel in the event that: (1) the interval between the reference time and the milestone time is less than a predetermined magnitude and (2) a variation greater than a predetermined magnitude exists between the reference resistance characteristic and the milestone resistance characteristic.

* * * * *